(12) United States Patent
Weber (10) Patent No.: US 8,172,104 B2
(45) Date of Patent: May 8, 2012

(54) MEDICAL WASTE DISPOSAL APPARATUS (75) Inventor: John A. Weber, Highland Park, IL (US)

(73) Assignee: John A. Weber, Highland Park, IL (US)

(*) Notice: Subject to any disclaimer, the term of this patent is extended or adjusted under 35 U.S.C. 154(b) by 704 days.

(21) Appl. No.: 12/283,680

(22) Filed: Sep. 15, 2008

(65) Prior Publication Data

US 2010/0069699 A1 Mar. 18, 2010

(51) Int. Cl.
B65D 75/14 (2006.01)
(52) U.S. Cl. .......... 220/62; 206/210; 206/364; 206/438
(58) Field of Classification Search .............. 206/210, 206/364, 365, 366, 438; 220/680, 62
See application file for complete search history.

(56) References Cited

U.S. PATENT DOCUMENTS

| | | | |
|---|---|---|---|
| 1,156,762 A | 10/1915 | Dickinson | |
| 2,990,059 A * | 6/1961 | Hitt | 206/365 |
| 3,727,749 A | 4/1973 | Martin | |
| 4,182,448 A * | 1/1980 | Huck et al. | 206/380 |
| 4,859,515 A * | 8/1989 | Pothetes | 428/41.7 |
| 4,875,896 A | 10/1989 | Kurtz | |
| 4,898,276 A | 2/1990 | Georgakis | |
| 4,917,243 A | 4/1990 | Abrams et al. | |
| 4,921,096 A | 5/1990 | McFarlane | |
| 4,927,076 A | 5/1990 | Simpson | |
| 4,966,591 A | 10/1990 | Yuen | |
| 4,969,554 A | 11/1990 | Sawaya | |
| 4,979,616 A | 12/1990 | Clanton | |
| 5,024,326 A | 6/1991 | Sandel et al. | |
| 5,031,768 A | 7/1991 | Fischer | |
| 5,046,612 A | 9/1991 | Mostarda et al. | |
| 5,090,564 A | 2/1992 | Chimienti | |
| 5,121,836 A * | 6/1992 | Brown et al. | 206/63.3 |
| 5,133,454 A | 7/1992 | Hammer | |
| 5,181,609 A | 1/1993 | Spielmann et al. | |
| 5,269,457 A | 12/1993 | De La Fuente | |
| 5,277,312 A | 1/1994 | Vumbaca | |
| 5,293,993 A | 3/1994 | Yates, Jr. et al. | |
| 5,336,193 A | 8/1994 | Rom et al. | |
| 5,361,781 A | 11/1994 | Antonini | |
| 5,375,717 A * | 12/1994 | Roshdy | 206/476 |
| 5,383,862 A * | 1/1995 | Berndt et al. | 604/187 |
| 5,402,886 A | 4/1995 | McGlinch | |
| 5,407,070 A | 4/1995 | Bascos et al. | |
| 5,417,926 A | 5/1995 | Bouveret | |

(Continued)

OTHER PUBLICATIONS

Written Opinion of International Search Authority, for PCT/US2009/56320, Oct. 23, 2009.

(Continued)

*Primary Examiner* — Mickey Yu
*Assistant Examiner* — Niki Eloshway
(74) *Attorney, Agent, or Firm* — Greenberg Traurig, LLP (57) ABSTRACT

A medical waste disposal apparatus for receiving and retaining waste articles, such as catheter fittings, and the like, for controlled and facilitated handling and disposal of such waste articles, during and following the performance of treatment procedures on a patient by a practitioner. The waste disposal apparatus includes a first retaining member, mounted on a base panel, for receiving and retaining a waste article placed there by a practitioner during a treatment procedure, and further includes at least one side panel, for covering the waste article, after placement of the waste article on the first retaining member. Alternative configurations of retaining members are provided.

11 Claims, 14 Drawing Sheets

U.S. PATENT DOCUMENTS

| | | | |
|---|---|---|---|
| 5,538,132 A * | 7/1996 | Propp et al. | 206/365 |
| 5,690,222 A | 11/1997 | Peters | |
| 5,758,775 A | 6/1998 | Lowe | |
| 5,938,063 A | 8/1999 | Hoftman | |
| 6,026,959 A | 2/2000 | Lowe | |
| 6,027,490 A | 2/2000 | Radford et al. | |
| 6,047,826 A | 4/2000 | Kalinski et al. | |
| 6,595,361 B2 * | 7/2003 | Sugama | 206/350 |
| 6,651,813 B2 | 11/2003 | Vallans et al. | |
| 7,694,813 B2 * | 4/2010 | Shalaby | 206/438 |
| 7,771,651 B1 * | 8/2010 | Shalaby | 422/22 |
| 2005/0040060 A1 * | 2/2005 | Andersen et al. | 206/363 |
| 2006/0032773 A1 | 2/2006 | Booker et al. | |
| 2007/0023309 A1 * | 2/2007 | Davis | 206/438 |
| 2008/0058736 A1 | 3/2008 | Reshamwala | |

OTHER PUBLICATIONS

International Search Report, for PCT/US2009/56320, Oct. 23, 2009.

* cited by examiner

MEDICAL WASTE DISPOSAL APPARATUS

BACKGROUND OF THE INVENTION

1. Field of the Invention

The present invention relates to medical waste disposal apparatus, and associated methods for making and using same.

2. The Prior Art

The handling and disposal of medical waste articles presents challenges which are not ordinarily encountered in the handling of conventional waste products arising from human activity. This is because human medical waste articles frequently may be contaminated with infectious material such as bacteria or viruses that can be communicated to other individuals, if the medical waste articles are not promptly and carefully disposed of, immediately following completion of their use. For example, it is potentially hazardous for used bandages, syringes, etc., to be left in an unattended state, following their use on or with a patient.

One situation in which the handling of contaminated materials becomes particularly troublesome, is in the treatment of patients who have intravenous catheters, particularly when the catheter is being changed or removed. Due to economics, it is typically the case that a nurse or other practitioner must address the changing or removal of catheters or related objects without assistance. In addition, because the ratio of patients to healthcare personnel tends to be high, there is some pressure placed on the nurses or other practitioners to maintain a brisk pace, with maximum available efficiency, as they go about their rounds, e.g., in a hospital floor.

As such, there are many factors which weigh into the process by which a patient's intravenous catheter may be removed or replaced, during which procedure, a wound may need to be bandaged, or at least a gauze and/or band-aid applied, and the removed/replaced catheter or similar appliance must be safely and sanitarily disposed of, with a minimum of effort and mess; all this while the nurse or other practitioner may have to hold a bandage or gauze in place to staunch bleeding while having to simultaneously address the disposal of the contaminated article. In addition, the resulting waste articles, such as a removed catheter fitting (possibly with still-attached tubing), may be accompanied with a wad of adhesive tape or transparent dressing, such as is often used to help maintain a difficult-to-secure catheter fitting in place while in service. Such wads of adhesive tape or dressings further complicate and render difficult the job of safely and efficiently disposing of such potentially contaminated medical waste articles.

It would therefore be desirable to provide a method and apparatus for the facilitated handling and disposal of catheters, catheter fittings and related articles, which may be contaminated with a patient's blood or other bodily fluids, as well as with disease-bearing contaminants.

It would further be desirable to provide such a method and apparatus in which the method for containment may be practiced, and the apparatus operated, in a one-handed manner.

These and other desirable characteristics of the present invention are discussed in detail herein, in conjunction with the present specification, claims and drawings.

SUMMARY OF THE INVENTION

The medical waste disposal apparatus, in an embodiment of the present invention comprises a base panel, having a first side and a second side. At least one side panel is disposed adjacent the base panel, and is movable between an open position, and a closed position over the first side of the base panel. A first retaining member is disposed on the first side of the base panel. The retaining member is operably configured to receive a waste article when the at least one side panel is in its open position, and hold the waste article in position adjacent the first side of the base panel, to enable the at least one side panel to be moved from its open position to its closed position, to capture the waste article within the medical waste disposal apparatus.

In an embodiment of the invention, the medical waste disposal apparatus comprises a base panel, having a first side and a second side. First and second side panels are movable between open and closed positions, and are disposed adjacent opposing side regions of the base panel, and operably configured to overlap one another, when they are disposed in their respective closed positions. First and second flaps are movable between open and closed positions. The first and second flaps are disposed substantially adjacent one another, proximate an end of the base panel, and are operably configured to intersect and partially overlap one another, when they are disposed in their respective closed positions.

A first retaining member is disposed on the first side of the base panel, and is operably configured to receive a waste article when the at least one side panel is in its open position, and to hold the waste article in position adjacent the first side of the base panel, to enable the at least one side panel to be moved from its open position to its closed position, to capture the waste article within the medical waste disposal apparatus.

The base panel includes an elongated rectangular region having a longitudinal axis, the first retaining member being operably disposed thereon, so that a waste article disposed thereon is maintained in alignment with the longitudinal axis of the base panel.

A second retaining member is disposed on the second side of the base panel, for maintaining the medical waste disposal apparatus in removable fixed positioning, relative to a desired location.

At least one stabilizing member is operably associated with the base panel and the at least one side panel, for enabling the at least one side panel to maintain a desired position, once placed in that position by a user of the apparatus.

DETAILED DESCRIPTION OF THE INVENTION

While this invention is susceptible of embodiment in many different forms, there is shown in the drawings, and described in detail herein, multiple embodiments, with the understanding that the present disclosure is to be considered an exemplification of the principles of the invention and is not intended to limit the invention to the embodiments illustrated.

The following description and drawings are illustrative and are not to be construed as limiting. Numerous specific details are described to provide a thorough understanding of the disclosure. However, in certain instances, well-known or conventional details are not described in order to avoid obscuring the description. References to one, or an, embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms may be provided. A recital of one or more synonyms does not exclude the use of other synonyms. The use of examples anywhere in this specification, including examples of any terms discussed herein, is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions, will control.

Figure 3:
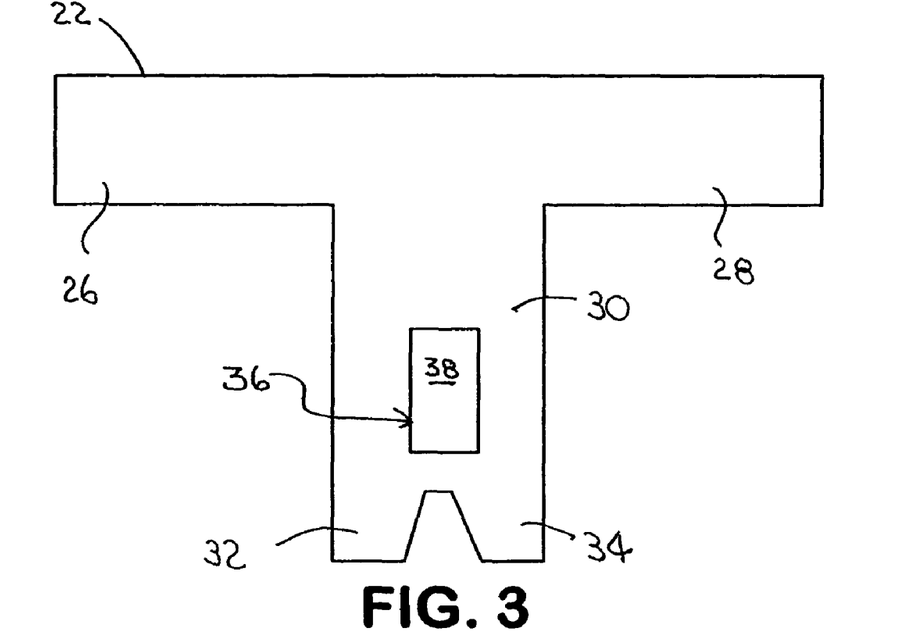
FIG. 3 is a top plan view of a material blank which may be used to fabricate a medical waste disposal apparatus according to the embodiments of FIGS. 1-2.
Figure 4:
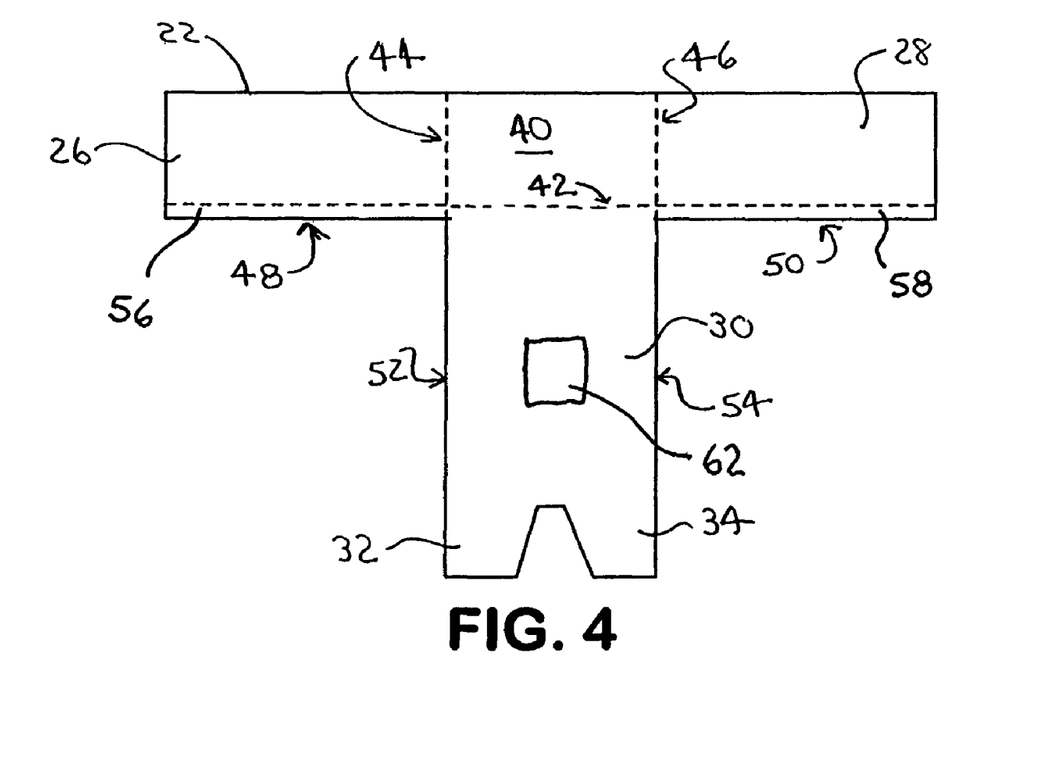
FIG. 4 is a bottom plan view of the material blank of FIG. 3.

Waste disposal apparatus 20 (FIGS. 1-2, 5-12) according to an embodiment of the invention, includes substrate 22 (FIGS. 3-4). Substrate 22 may be fabricated from any suitable material, which has as one of its characteristics an ability to retain a position or configuration, once placed in that position or configuration. Such materials may include metal (e.g., aluminum) or plastic sheet material of a suitable thickness, corrugated paperboard material (e.g., g-flute or other narrow-gauge flute corrugated paperboard material, including such material coated to resist passage of moisture or liquids therethrough), or thin plastic or paper material.

For example, in an embodiment of the invention, substrate 22 may be fabricated from barrier sheet material, such as may be commonly employed in hospital environments, which barrier sheet material may be a synthetic sheet material, which is either inherently waterproof, or which may be suitably treated to resist passage of liquids, and which further may be provided with a layer of liquid absorbing material on one side. In the environment of the present invention, such a liquid absorbing layer may be provided on the "inside" surface of substrate 22; that is, the side of substrate 22, which is facing the observer of FIG. 3.

In the embodiment of the preceding paragraph, to provide the position or configuration retaining characteristic, stabilizing members 24 may be embedded within, or attached to, one or both sides of substrate 22, e.g., on the "outside" surface of substrate 22; that is, the side of substrate 22, which is facing the observer of FIG. 4. Stabilizing members 24 may be metal strips or wire, or other "memory" retaining materials.

In an embodiment of the invention, substrate 22 is fabricated in a "T" shape, as illustrated in FIGS. 3 and 4, with arms 26, 28; leg 30; and flaps 32, 34. Stabilizing members 24, in this embodiment of the invention, have not yet been attached to substrate 22, for reasons that will become apparent. In addition, a retaining member 36 is positioned on the "inside"

surface of leg 30. Retaining member 36, in an embodiment of the invention, may comprise a strip of double-sided adhesive tape, which is provided with a protective sheet 38, for covering the adhesive surface of the tape that is not adhered to substrate 22, until desired, as described in further detail hereinbelow.

Figure 5:
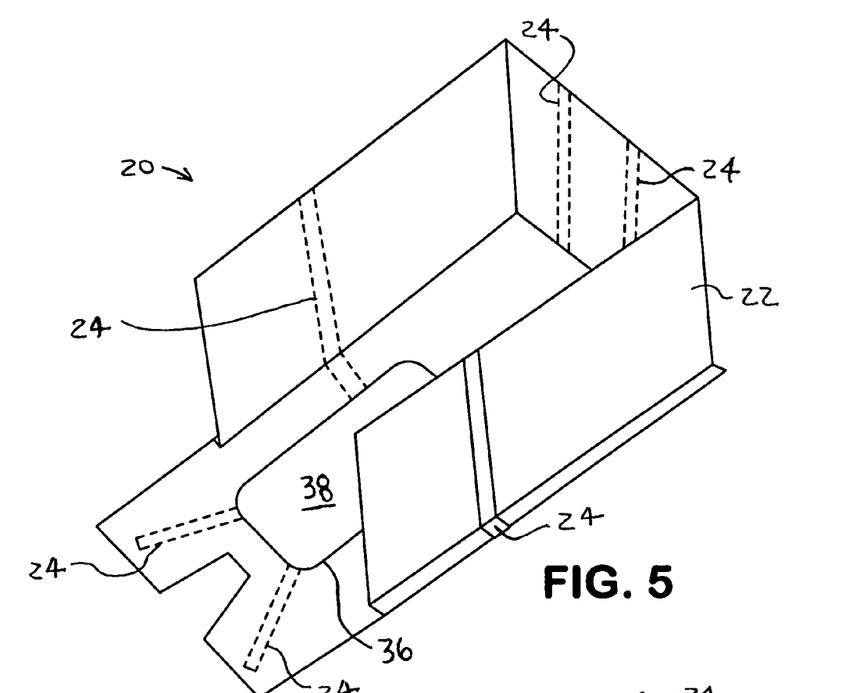
FIG. 5 is a top perspective view of the medical waste disposal apparatus of FIGS. 1-2, shown in its deployed configuration.
Figure 6:
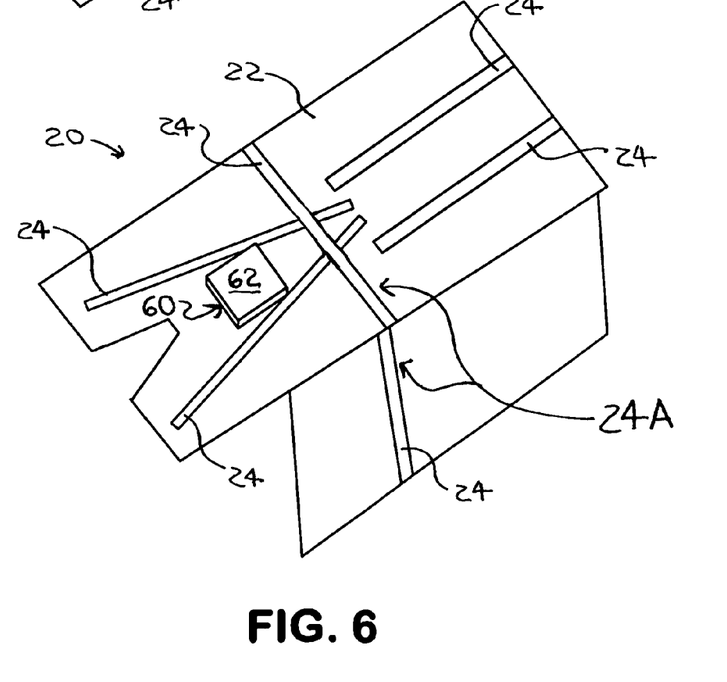
FIG. 6 is a bottom perspective view of the medical waste disposal apparatus of FIG. 5.

Formation of substrate 22 into waste disposal apparatus 20 begins with the folding of substrate 22 into the configuration shown in FIGS. 5 and 6. Panel 40 is folded to a position more or less perpendicular to leg 30 (away from the observer of FIG. 4), along a fold line positioned generally in the vicinity of dotted line 42 of FIG. 4. Arms 26, 28 are then folded perpendicular to panel 40, generally in the vicinity of dotted lines 44, 46, respectively, so that edges 48, 50 may be aligned with edges 52, 54, respectively. Regions 56, 58 may then be affixed to corresponding areas of the "inside" surface (FIG. 3) of leg 30, by any suitable means, such as adhesive, sonic or thermal bonding, etc.

The resulting structure (with the subsequent addition of stabilizing members 24) is shown in FIGS. 5 and 6. In an embodiment of the invention, stabilizing member 24A (FIG. 4) comprises a single continuous strip or wire which extends from arm 26, across leg 30, and into arm 28. Such a single continuous strip or wire can be attached to an outside or inside surface of substrate 22, after substrate 22 has been formed into the shape shown in FIGS. 5 and 6. Alternatively, stabilizing member 24A may be formed from three separate strips or wires which are suitably positioned on arms 26, 28 and leg 30, so as to align as illustrated, following the folding and affixation of substrate 22 into the configuration shown in FIGS. 5 and 6. Such separate strips or wires may be affixed, to an inside or outside surface of substrate 22, prior to folding of substrate 22, or may be embedded within substrate 22.

A further retaining member 60, which may likewise be in the form of a double-sided adhesive tape, having a protective sheet 62, is, in an embodiment of the invention, positioned on the outside surface of leg 30, which, during use of waste disposal apparatus 20, is the "bottom" side of the apparatus. In an alternative embodiment of the invention, retaining member may be in the form of a sheet of hook-and-loop fastener material, for gripping onto fabric-covered surfaces. In another alternative, magnets may be employed, e.g., to enable the temporary placement of waste disposal apparatus against the metal surface of the side of a hospital bed or table or the like. Other retaining member structures may be employed, by one of ordinary skill in the art having the instant disclosure before them, without departing from the scope of the present invention.

Figure 1:
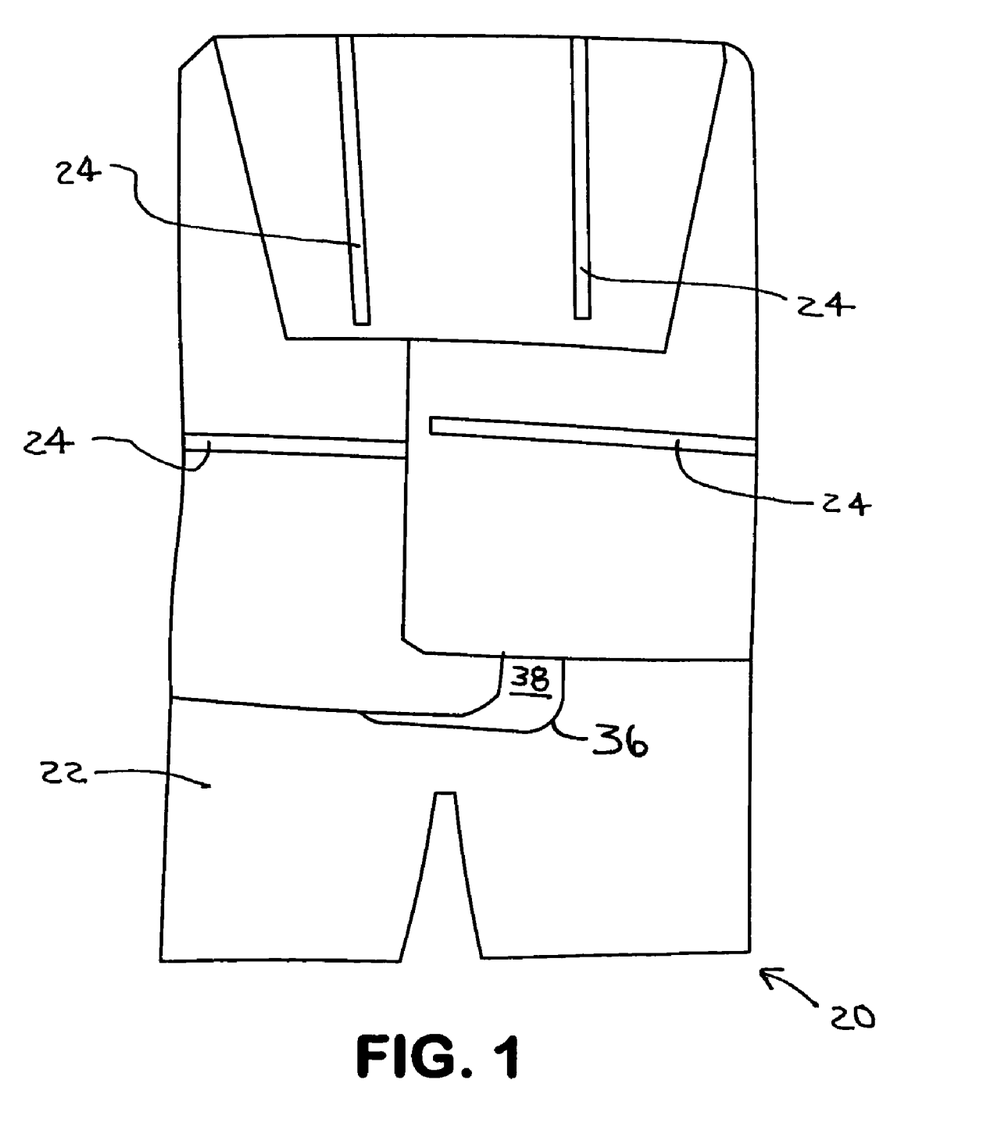
FIG. 1 is a top plan view of a medical waste disposal apparatus according to an embodiment of the invention, shown in its closed configuration prior to deployment and use.
Figure 2:
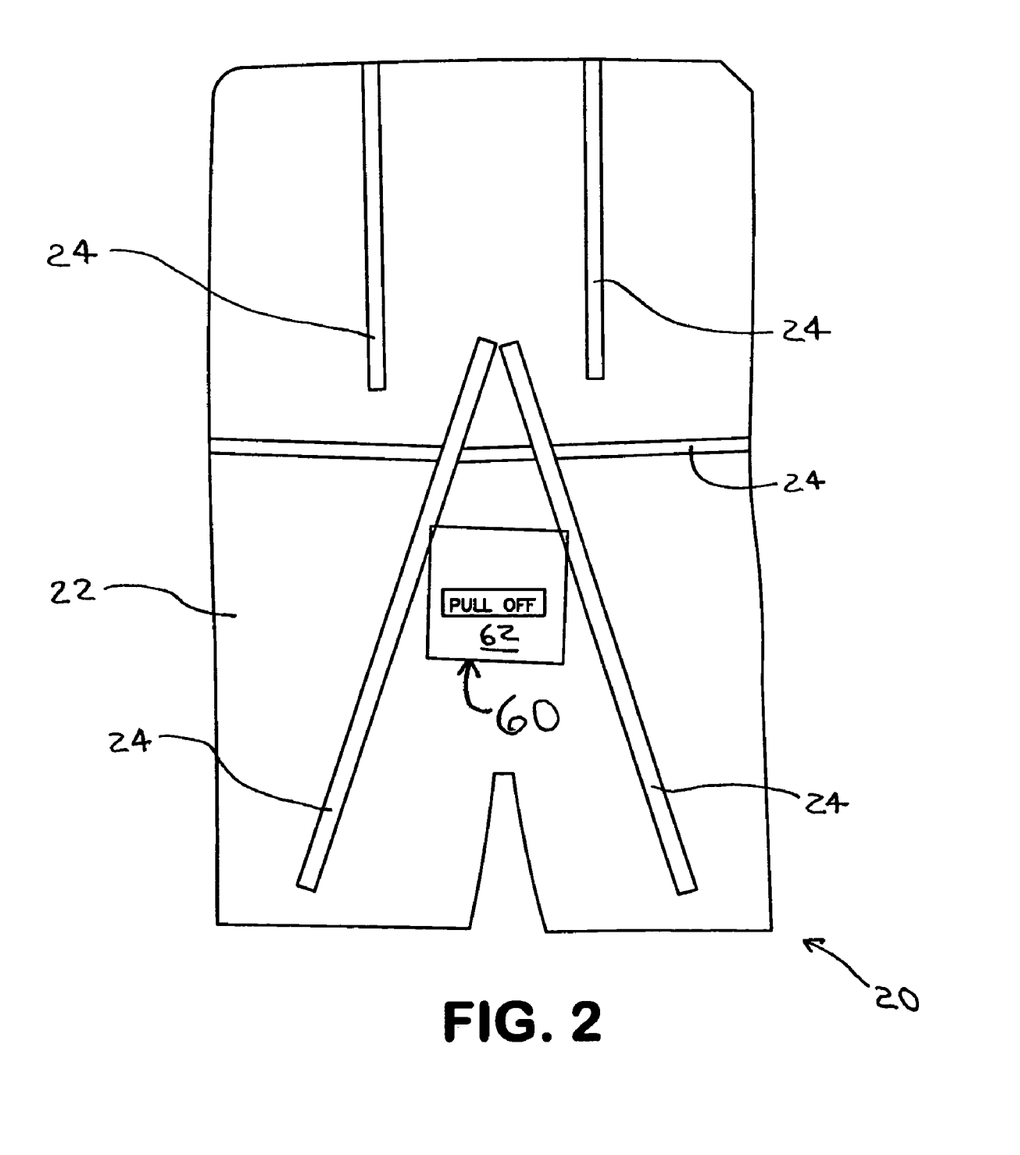
FIG. 2 is a bottom plan view of the medical waste disposal apparatus according to the embodiment of FIG. 1.

Following formation of waste disposal apparatus 20, as described hereinabove, waste disposal apparatus may be folded into the configuration shown in FIG. 1, for compactness for packaging and transportation. In such a configuration, ancillary materials, such as prepackaged sanitary gauze pads, band-aids, tape strips and/or packaged sanitary antiseptic wipes, may be placed within waste disposal apparatus 20, prior to folding up of waste disposal apparatus 20, to create, e.g., a catheter removal kit.

Figure 7:
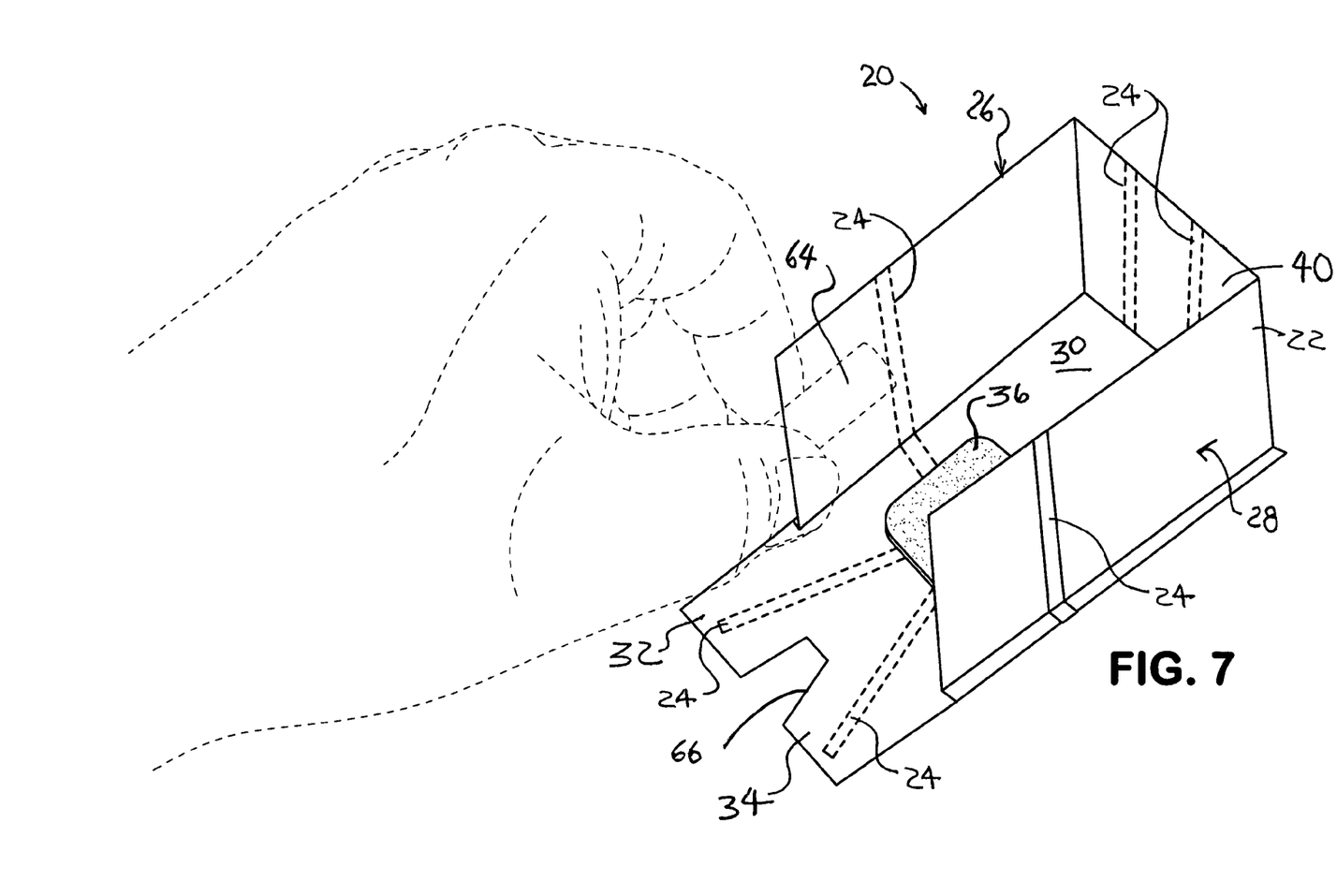
FIG. 7 is a top perspective view, similar to that of FIG. 5, wherein an article of potentially contaminated medical wastes is initially being positioned on a retaining pad disposed within a medical waste disposal apparatus according to an embodiment of the invention.
Figure 8:
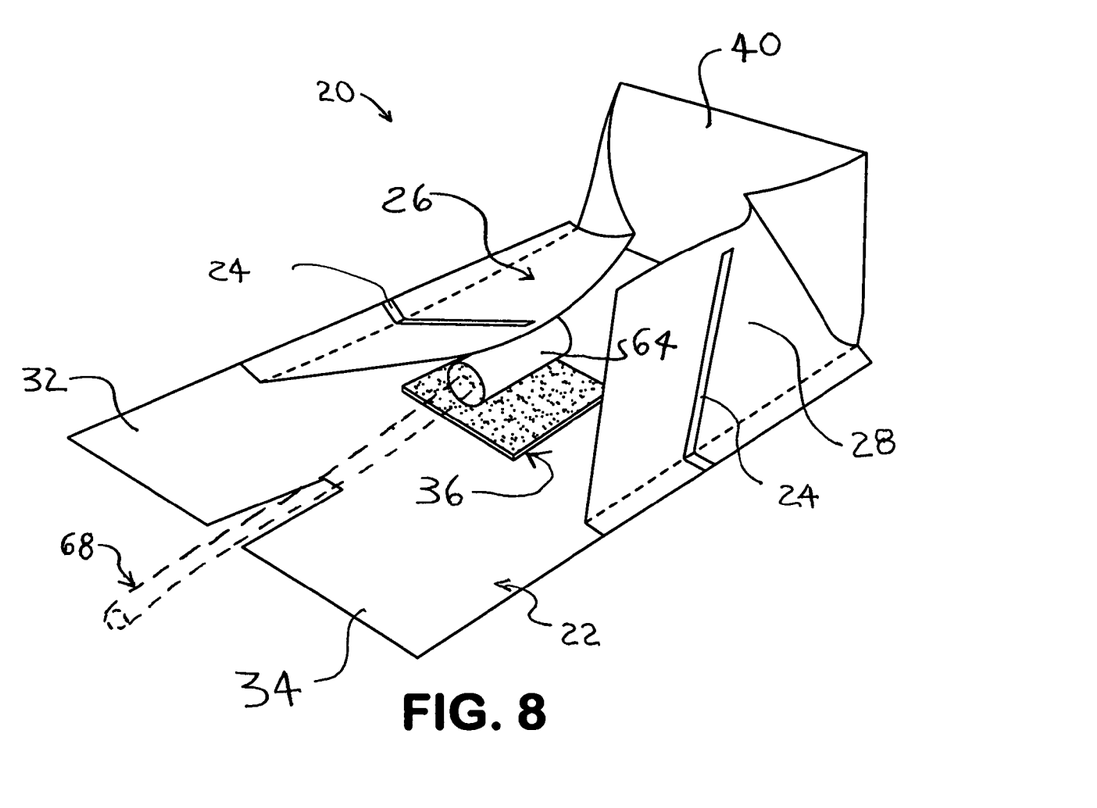
FIG. 8 is a perspective view of the medical waste apparatus of FIG. 7, following placement of an article of medical waste on the retaining pad, showing how a first side of the medical waste apparatus is folded downwardly over the article of medical waste.
Figure 9:
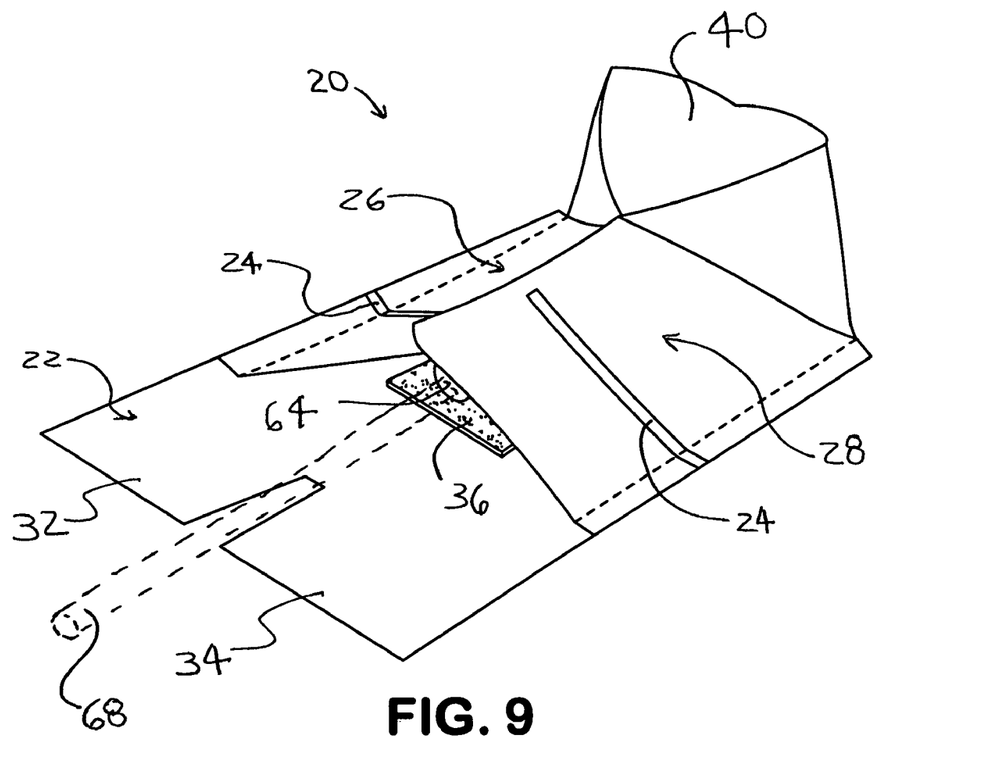
FIG. 9 is a perspective view of the medical waste apparatus of FIGS. 7-8, following the step shown in FIG. 8, wherein an opposite side of the medical waste apparatus is subsequently folded down over the folded-down first side of the apparatus.
Figure 10:
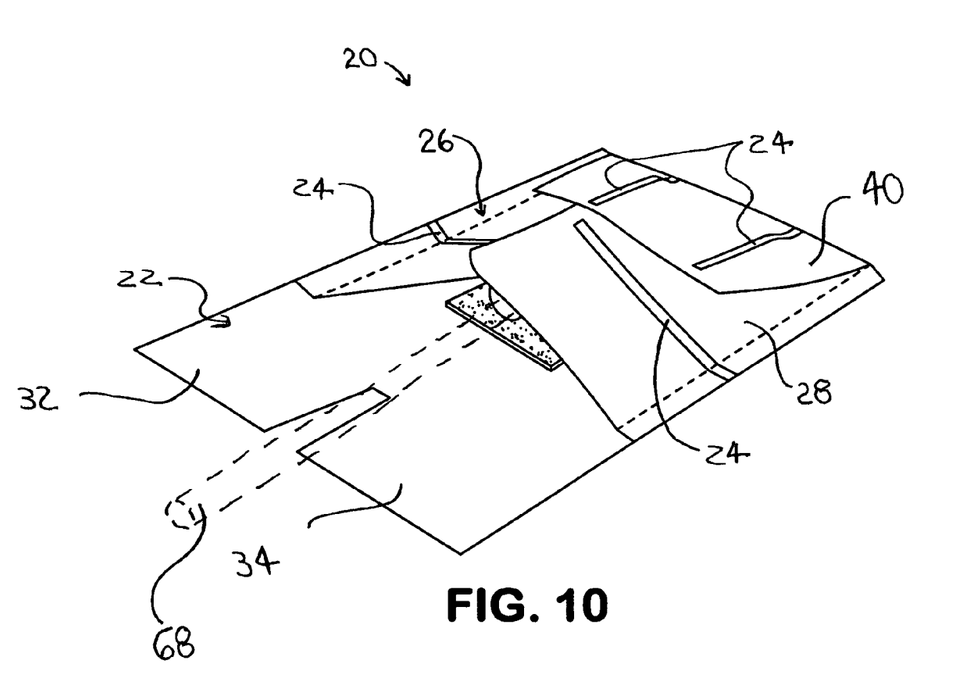
FIG. 10 is a perspective view of the medical waste apparatus of FIGS. 7-9, following the step shown in FIG. 9, wherein a front end portion of the medical waste apparatus is subsequently folded down over the previously folded-down sides of the apparatus, over an article of medical waste.
Figure 11:
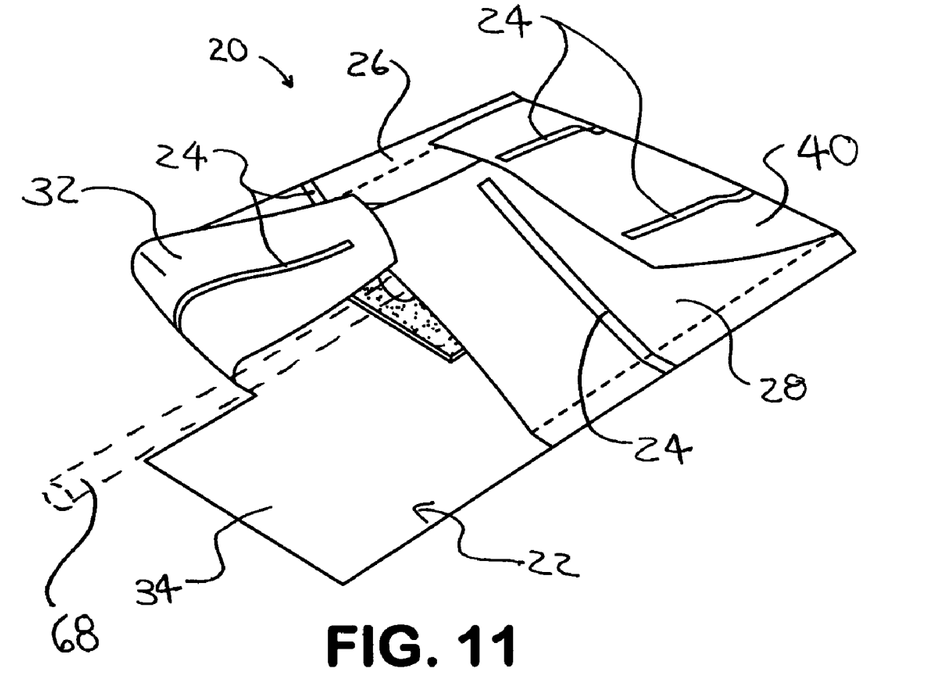
FIG. 11 is a perspective view of the medical waste apparatus of FIGS. 7-10, following the step shown in FIG. 10, wherein a first flap portion of the medical waste apparatus is subsequently folded up over the already folded down sides of the medical waste apparatus.
Figure 12:
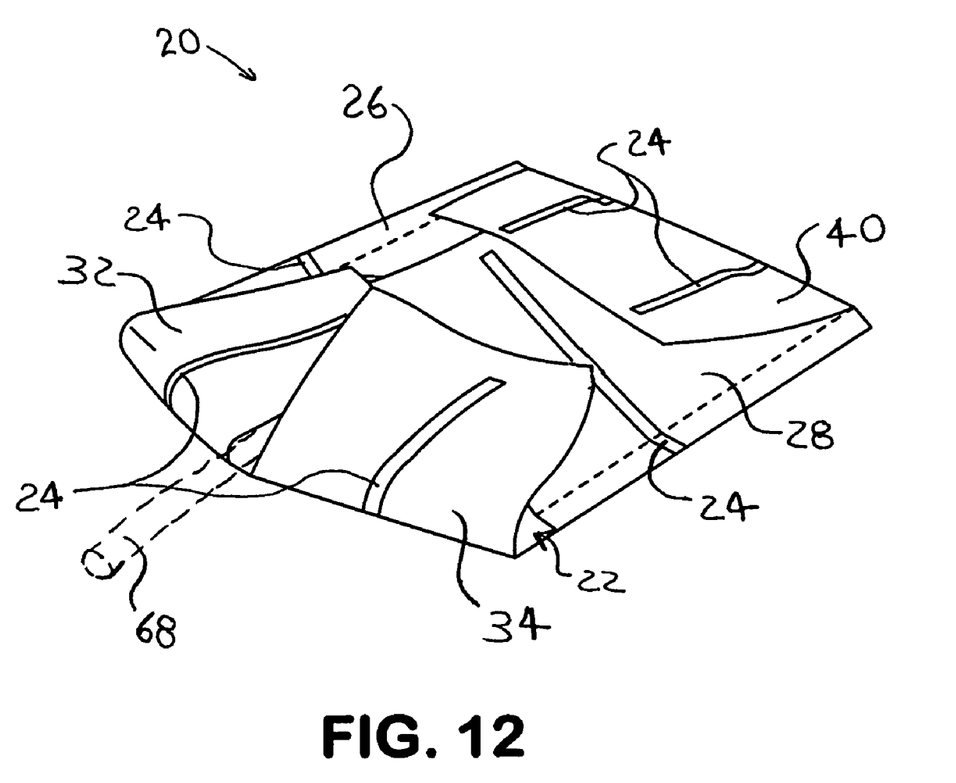
FIG. 12 is a perspective view of the medical waste apparatus of FIGS. 7-11, following the step shown in FIG. 11, wherein a second flap portion of the medical waste apparatus is subsequently folded up over the first flap portion as well as over the already folded down sides of the medical waste apparatus.
Figure 13:
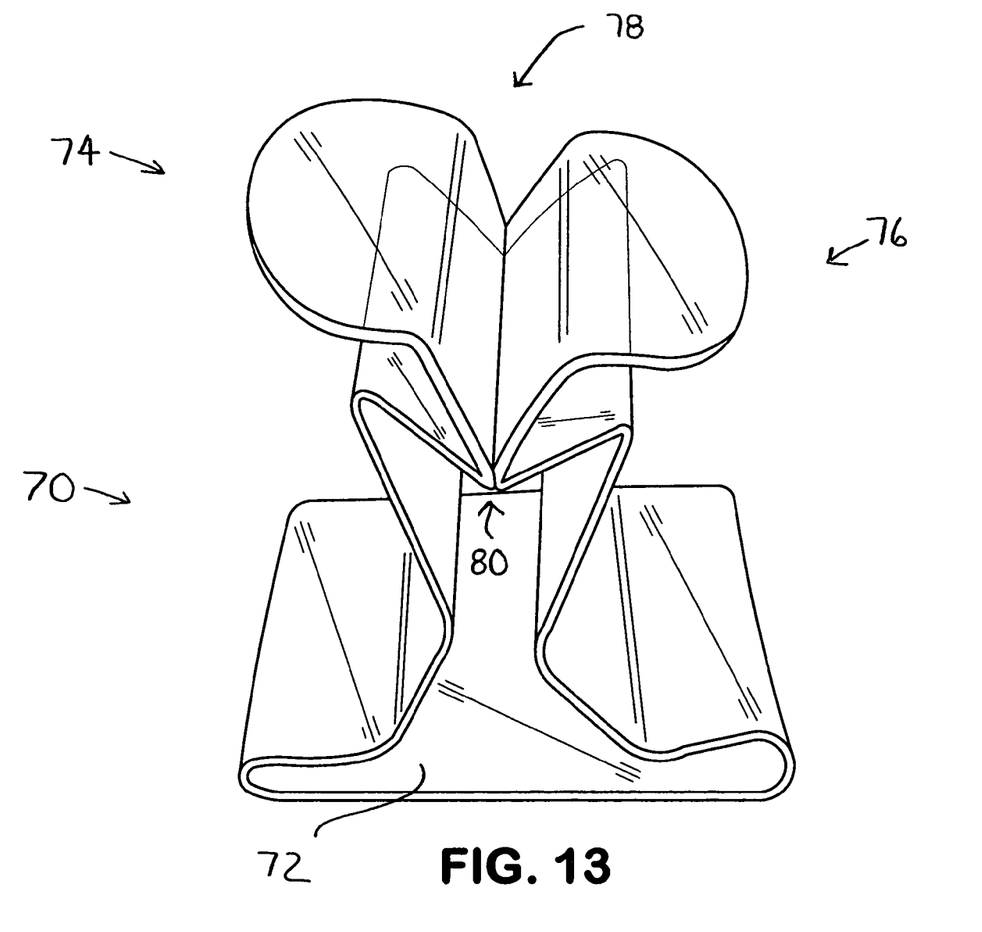
FIG. 13 is an end perspective view of a further medical waste disposal apparatus, according to another embodiment of the invention, which may be used separately or in conjunction with the medical waste disposal apparatus according to the embodiment(s) of the previous figures.

In use, a practitioner first removes protective sheet 62, and places waste disposal apparatus 20 at any convenient location, such as on a clear space on a patient's bed (not shown), so that retaining member 60 adheres to the bedding of the bed. The practitioner then opens up waste disposal apparatus 20, by first lifting up arm 28, and then arm 26, to the positions shown in FIG. 7, causing panel 40 to likewise assume the orientation shown in FIG. 7. The practitioner then removes protective sheet 38 from retaining member 36. The practitioner then performs the required activity for the patient, e.g., the removal of a catheter (or other preferably non-sharp containing object) from a patient's body, and places the waste article 64 (FIG. 7) onto the now-exposed adhesive surface of retaining member 36. The waste article 64 may have tubing (not shown in FIG. 7, shown in FIGS. 8-12) attached. Waste article 64 preferably will be placed by the practitioner on retaining member 36 in such a way that the tubing will be aligned with notch 66, which separates and defines flaps 32, 34.

Once waste article 64 has been temporarily secured on retaining member 36, it is then covered by folding down arms 26 (FIG. 8), arm 28 (FIG. 9), followed by panel 40 (FIG. 10), then flaps 32 (FIG. 11) and 34 (FIG. 12), to substantially completely enclose waste article 64. It is to be understood that the foregoing sequence of steps is but one possible sequence, which may be employed, in capturing and enclosing waste article 64, within waste disposal apparatus 20, and that other sequences may be employed, without departing from the scope of the present invention.

The practitioner may then dispose of the trapped waste article 64, and waste disposal apparatus 20, in any suitable and convenient manner.

FIGS. 13-16 illustrate a retaining member 70, which may be used separately or in conjunction with the waste disposal apparatus 20 of FIGS. 1-12. In an embodiment of the invention, retaining member 70 comprises a spring clip, which may be fabricated from any suitable resilient material, such as plastic or metal, and which includes a base 72, from which two wings 74, 76 emanate. Wings 74, 76 are preferably contoured to form an entry or receiving region 78, and a gripping region 80.

Figure 14:
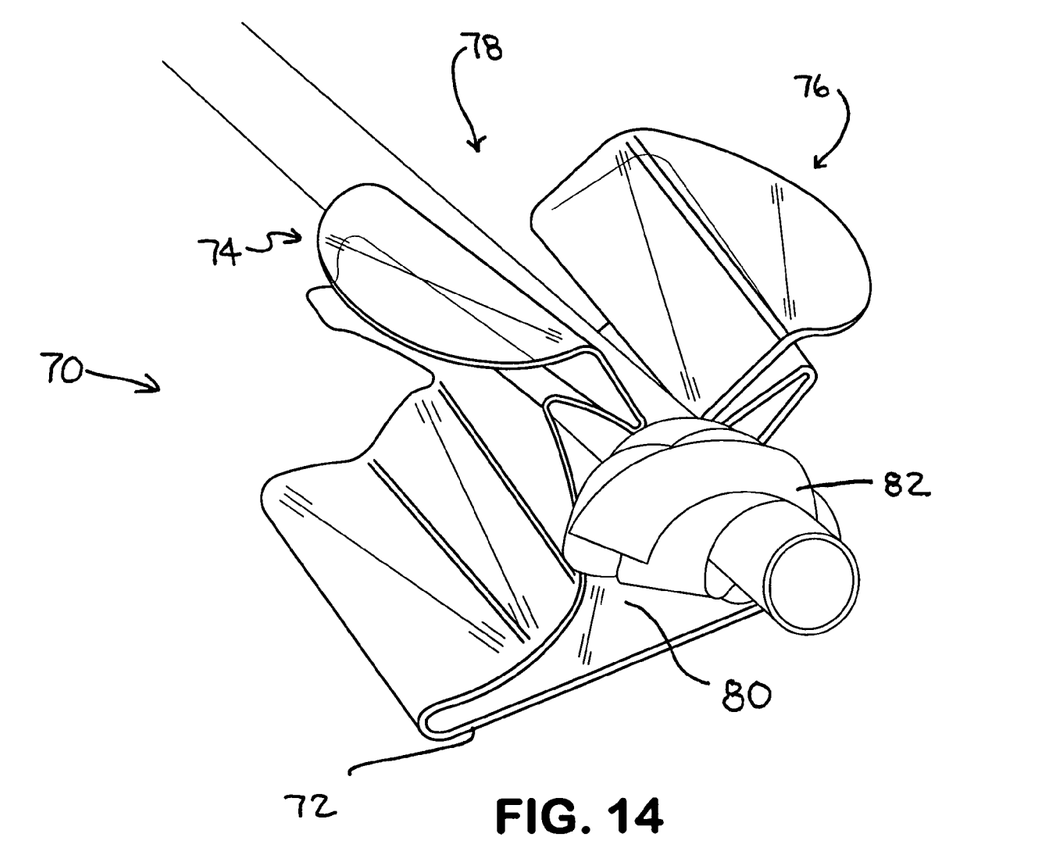
FIG. 14 is a top, side perspective view of the medical waste disposal apparatus of FIG. 13, showing how a waste article, e.g., a catheter with accumulated gauze and/or tape, can be captured within a receiving region of the medical waste disposal apparatus.
Figure 15:
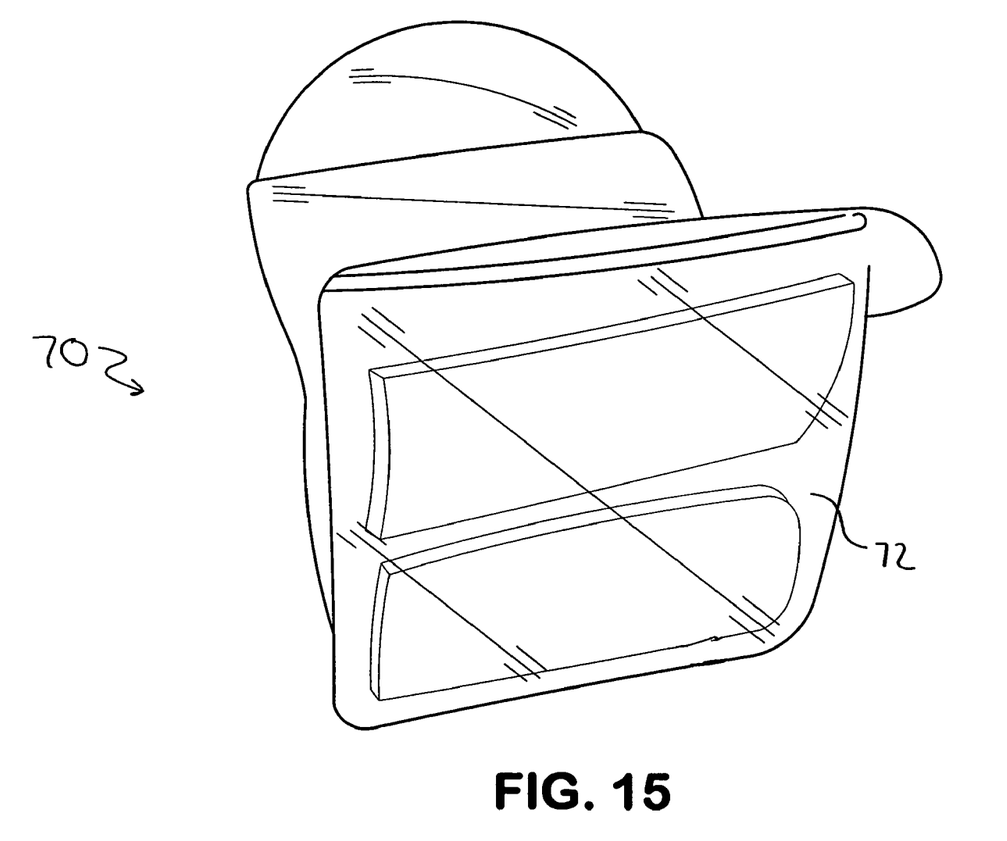
FIG. 15 is a bottom perspective view of the medical waste apparatus of FIGS. 13-14.
Figure 16:
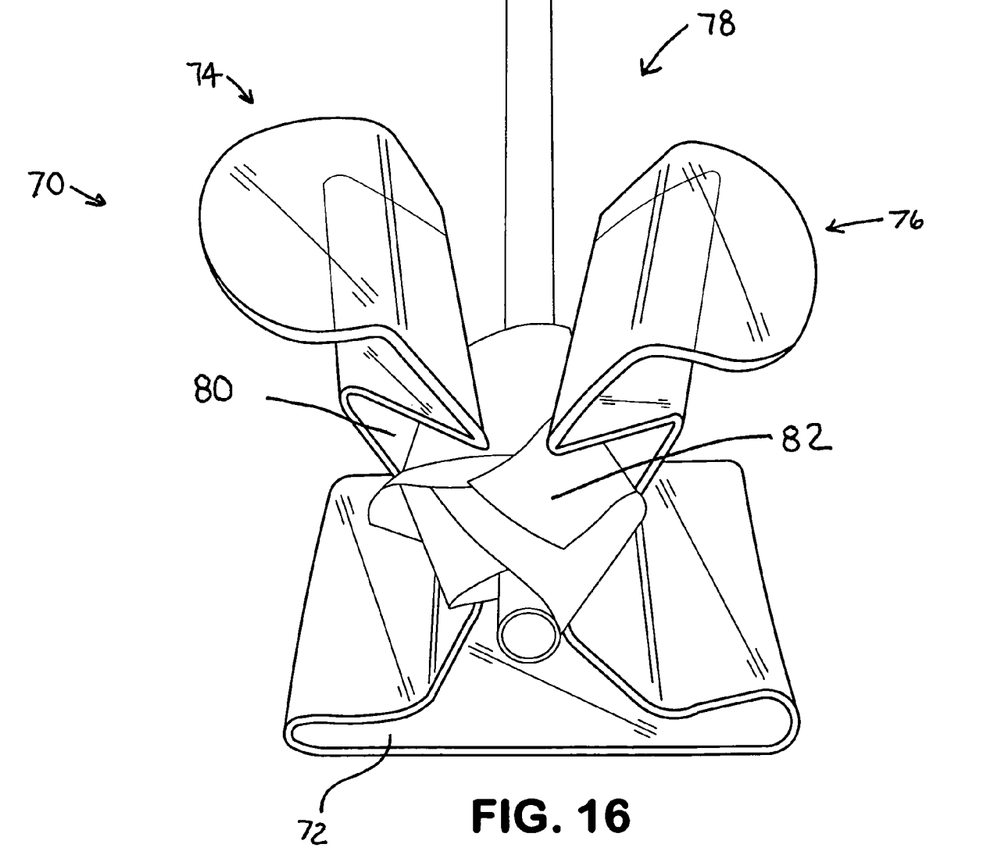
FIG. 16 is an end elevation of the medical waste disposal apparatus of FIGS. 13-15, showing how a waste article, e.g., a catheter with accumulated gauze and/or tape, can be captured within a receiving region of the medical waste disposal apparatus.

Retaining member 70 may be used in combination with waste disposal apparatus 20, by positioning retaining member 70 on retaining member 36. That is, base 72 may be adhesively adhered to retaining member 36 following removal of protective sheet 38. A practitioner simply may place a waste article 82 in retaining member 70, by positioning it in entry or receiving region 78, and pressing downwardly, until wings 74, 76 separate a sufficient distance to enable waste article 82 to enter and be captured within gripping region 80. FIGS. 14 and 16, for example, schematically illustrate an article, such as a catheter, surrounded by an accumulation of gauze and/or bandage tape, being received within gripping region 80.

Alternatively, retaining member 70 may be employed in a standalone mode, to receive and retain waste articles, and facilitate their safe handling and disposal. A retaining mechanism, in the form of a double-sided tape, or hook-and-loop style fastener or other suitable structure, may be placed on the bottom of base 72, to enable the retaining member 70 to be removably, securely positioned in place, e.g., on a patient's bedding.

The foregoing description and drawings merely explain and illustrate the invention, and the invention is not limited thereto, except as those skilled in the art who have the present disclosure before them will be able to make modifications and variations therein without departing from the scope of the invention.

What is claimed is:

1. A medical waste disposal apparatus, comprising:
   a base panel, having a first side and a second side;
   at least one side panel, disposed adjacent the base panel, and movable between an open position, and a closed position over the first side of the base panel;
   a first retaining member disposed on the first side of the base panel, the retaining member being operably configured to receive a waste article when the at least one side panel is in its open position, and hold the waste article in position adjacent the first side of the base panel, to enable the at least one side panel to be moved from its open position to its closed position, to capture the waste article within the medical waste disposal apparatus; and at least one selectively repositionable stabilizing member, operably associated with the base panel and at least one of the at least one side panel, for enabling the at least one side panel to be placed into maintained in and subsequently moved from, any one of a plurality of desired positions, relative to the base panes once said at least one side panel is placed into said one position by a user of the apparatus.

2. The medical waste disposal apparatus according to claim 1, wherein the base panel comprises an elongated rectangular region having a longitudinal axis, the first retaining member being operably disposed thereon, so that a waste article disposed thereon is maintained in alignment with the longitudinal axis of the base panel.

3. The medical waste disposal apparatus according to claim 1, wherein the at least one side panel comprises first and second side panels, disposed adjacent opposing side regions of the base panel, operably configured to overlap one another, when they are disposed in their respective closed positions.

4. The medical waste disposal apparatus according to claim 1, wherein the at least one side panel comprises first and second flaps, disposed substantially adjacent one another, proximate an end of the base panel, and operably configured to intersect and partially overlap one another, when they are disposed in their respective closed positions.

5. The medical waste disposal apparatus according to claim 1, wherein the first retaining member comprises a strip of double-sided adhesive tape.

6. The medical waste disposal apparatus according to claim 1, wherein the first retaining member comprises a resilient clip structure.

7. The medical waste disposal apparatus according to claim 1, further comprising a second retaining member, disposed on the second side of the base panel, for maintaining the medical waste disposal apparatus in removable fixed positioning, relative to a desired location.

8. The medical waste disposal apparatus according to claim 1, wherein the at least one stabilizing member comprises at least one plastically deformable elongated metal member operably disposed on and affixed to a side of at least one of the base panel and the at least one side panel.

9. The medical waste disposal apparatus according to claim 1, wherein the base panel and at least one side panel are monolithically formed from a single substrate.

10. The medical waste disposal apparatus according to claim 1, wherein the base panel and at least one side panel are formed from a multi-ply sheet having an absorbent layer and a liquid-impermeable layer.

11. A medical waste disposal apparatus, comprising:

a base panel, having a first side and a second side;

first and second side panels, movable between open and closed positions, the first and second side panels being disposed adjacent opposing side regions of the base panel, operably configured to overlap one another, when they are disposed in their respective closed positions;

first and second flaps, movable between open and closed positions, the first and second flaps being disposed substantially adjacent one another, proximate an end of the base panel, and operably configured to intersect and partially overlap one another, when they are disposed in their respective closed positions;

a first retaining member disposed on the first side of the base panel, the retaining member being operably configured to receive a waste article when the at least one side panel is in its open position, and hold the waste article in position adjacent the first side of the base panel, to enable the at least one side panel to be moved from its open position to its closed position, to capture the waste article within the medical waste disposal apparatus;

the base panel including an elongated rectangular region having a longitudinal axis, the first retaining member being operably disposed thereon, so that a waste article disposed thereon is maintained in alignment with the longitudinal axis of the base panel;

a second retaining member, disposed on the second side of the base panel, for maintaining the medical waste disposal apparatus in removable fixed positioning, relative to a desired location; and at least one selectively repositionable stabilizing member, operably associated with the base panel and at least one of the at least one side panel, for enabling the at least one side panel to be placed into, maintained in, and subsequently moved from, any one of a plurality of desired positions, relative to the base panel, once said at least one side panel is placed into said one position by a user of the apparatus.

* * * * *